(12) United States Patent
Kadykowski et al.

(10) Patent No.: US 8,372,096 B2
(45) Date of Patent: Feb. 12, 2013

(54) RING VESSEL DISSECTOR/HARVESTER DEVICE

(75) Inventors: Randal James Kadykowski, South Lyon, MI (US); Lyne Madeleine Charron-Keller, Brighton, MI (US)

(73) Assignee: Terumo Cardiovascular Systems, Ann Arbor, MI (US)

( * ) Notice: Subject to any disclaimer, the term of this patent is extended or adjusted under 35 U.S.C. 154(b) by 1668 days.

(21) Appl. No.: 11/710,370

(22) Filed: Feb. 23, 2007

(65) Prior Publication Data

US 2008/0208192 A1 Aug. 28, 2008

(51) Int. Cl.
*A61B 17/22* (2006.01)
*A61B 18/14* (2006.01)

(52) U.S. Cl. ............ 606/159; 606/49
(58) Field of Classification Search ............ 600/36; 606/27, 32–33, 39–41, 45–46, 49, 159, 167, 606/170, 190
See application file for complete search history.

(56) References Cited

U.S. PATENT DOCUMENTS

| 6,019,771 | A | * | 2/2000 | Bennett et al. | 606/159 |
| 6,281,262 | B1 | * | 8/2001 | Shikinami | 523/105 |
| 2003/0055417 | A1 | * | 3/2003 | Truckai et al. | 606/27 |
| 2005/0010242 | A1 | | 1/2005 | Lindsay | |
| 2005/0159764 | A1 | | 7/2005 | Kasahara et al. | |
| 2005/0192613 | A1 | | 9/2005 | Lindsay | |

\* cited by examiner

*Primary Examiner* — S. Thomas Hughes
*Assistant Examiner* — Ashley Cronin
(74) *Attorney, Agent, or Firm* — Gael Diane Tisack, Esq.; Darryl Newell; Macmillan, Sobanski & Todd

(57) ABSTRACT

A ring dissector/harvester device for dissecting and harvesting a vessel has a capture tool that is co-axially positioned around the vessel to at least temporarily hold the vessel. A sealing tool is coaxially positioned within the capture tool and is axially movable with respect to the capture tool. The sealing tool and the capture tool are engaged to cauterize a branch from the vessel and to seal the cauterized branch and vessel.

20 Claims, 3 Drawing Sheets

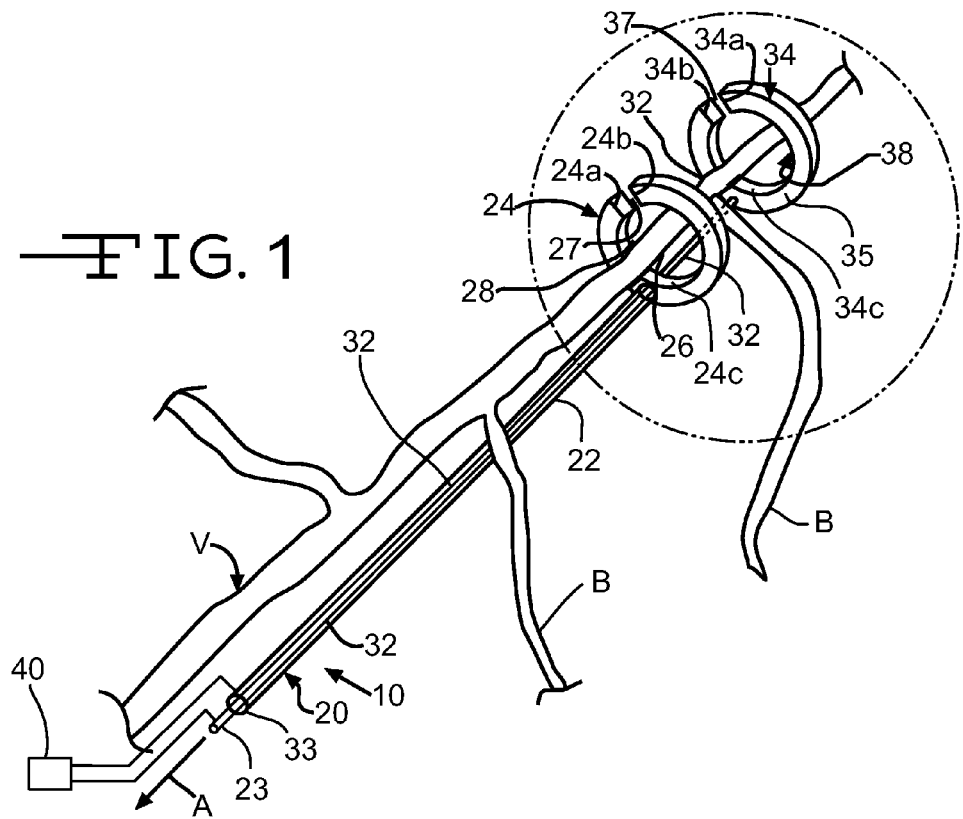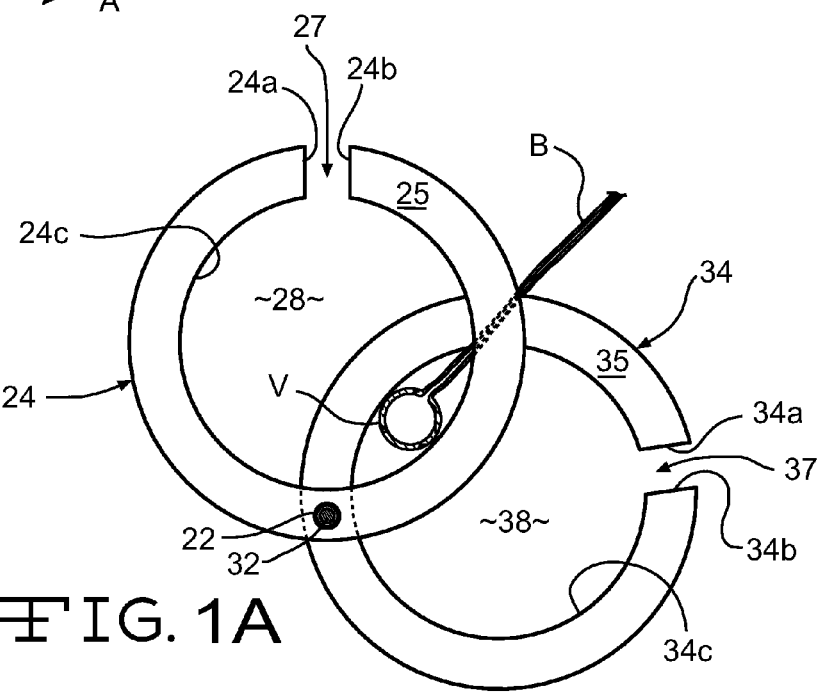

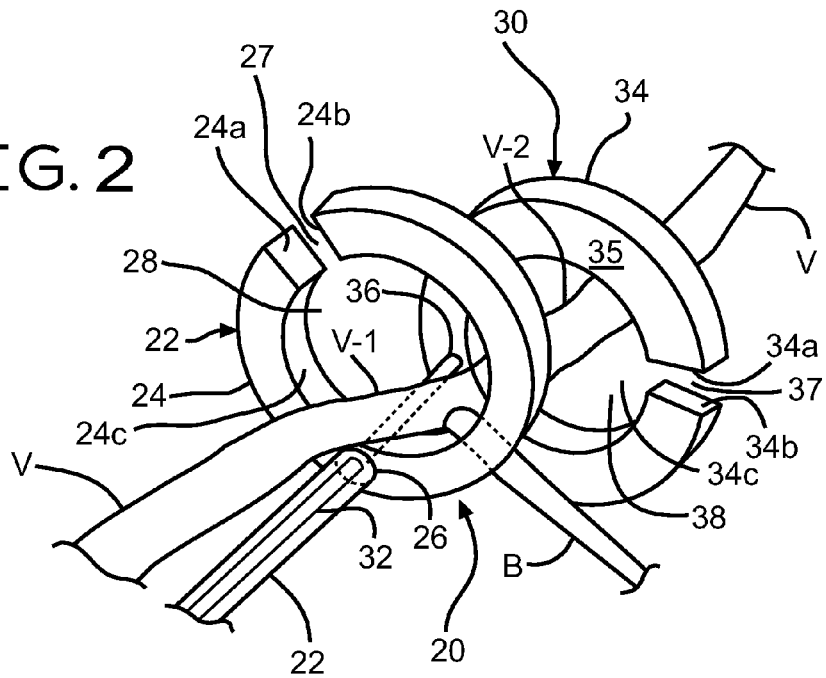
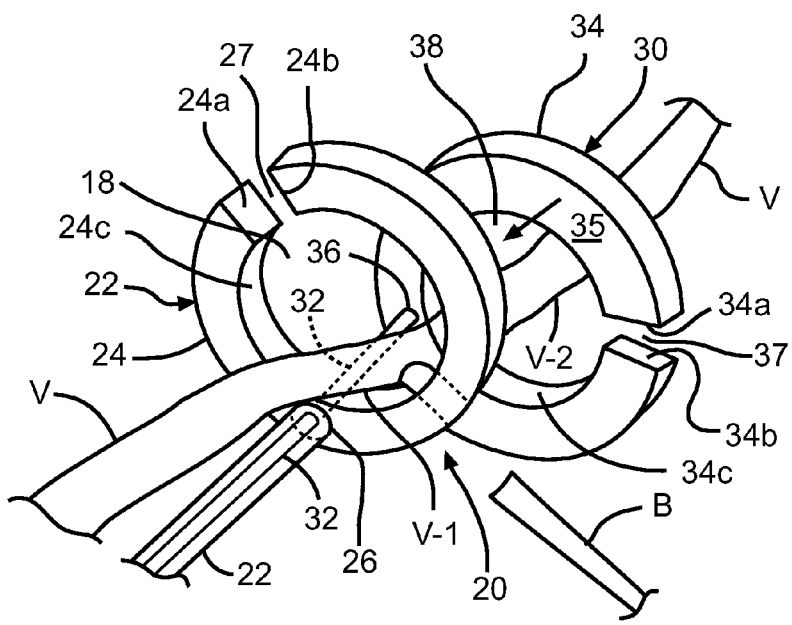

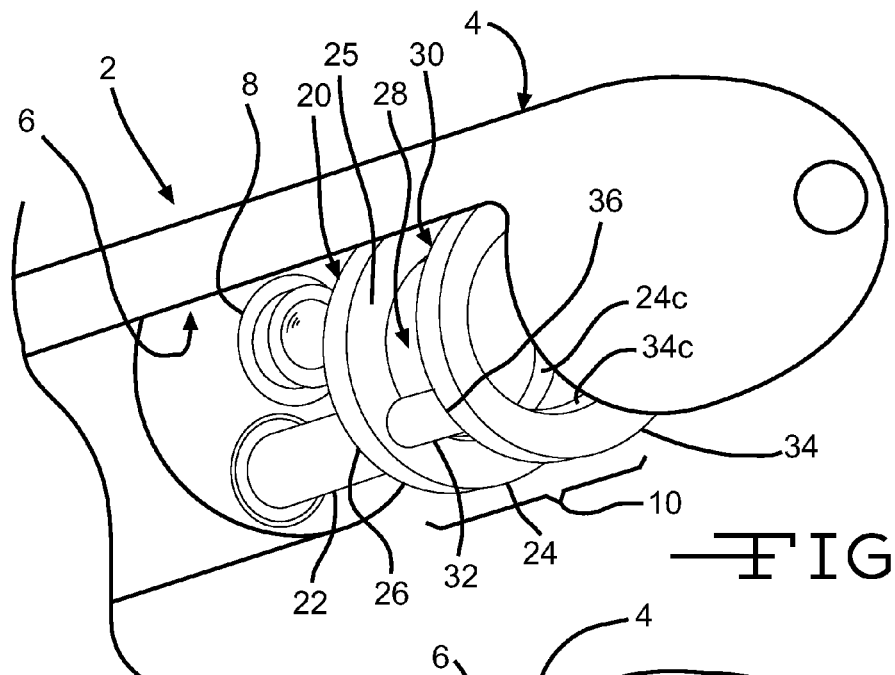
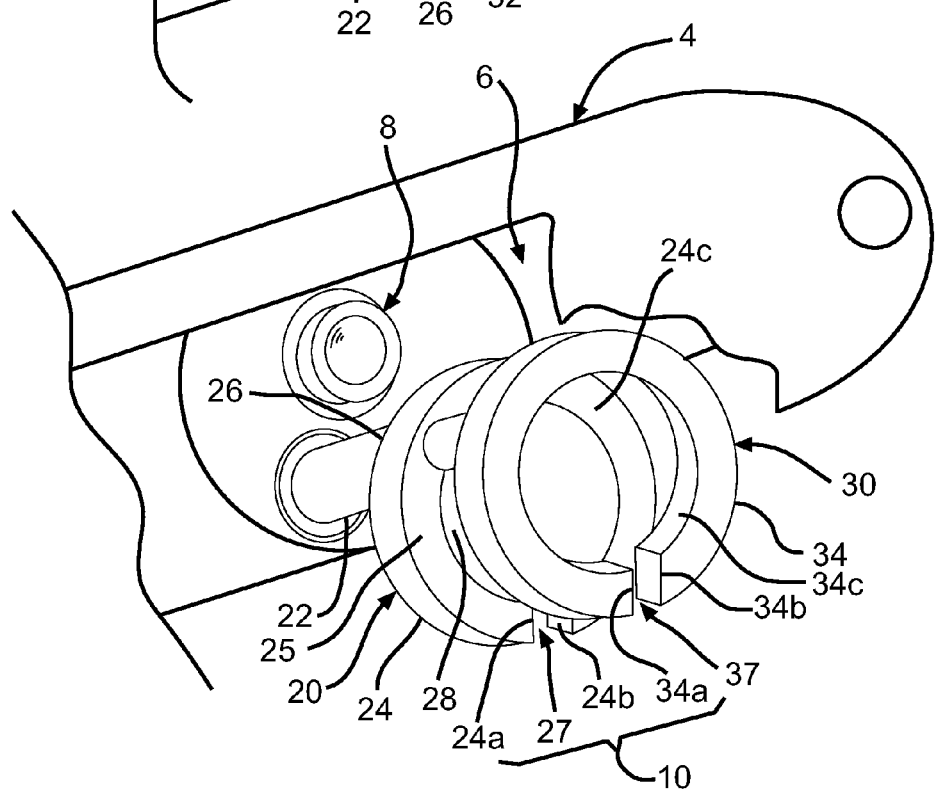

RING VESSEL DISSECTOR/HARVESTER DEVICE

CROSS-REFERENCE TO RELATED APPLICATIONS

Not applicable.

STATEMENT REGARDING SPONSORED RESEARCH

Not applicable.

BACKGROUND OF THE INVENTION

The present invention relates to the harvesting of blood vessels and, more particularly, to a method and apparatus for endoscopic dissection and retraction of sections of blood vessels for use as a coronary artery bypass graft.

In connection with coronary artery bypass grafting (CABG), a blood vessel or vessel section, such as an artery or vein, is "harvested" (i.e., removed) from its natural location in a patient's body and is used elsewhere in the body. In CABG surgery, the harvested blood vessel is used to form a bypass between an arterial blood source and the coronary artery that is to be bypassed. Among the preferred sources for the vessels to be used as the bypass graft are the saphenous vein in the leg and the radial artery in the arm.

Endoscopic surgical procedures for harvesting a section of a blood vessel (e.g., the saphenous vein) subcutaneously have been developed in order to avoid disadvantages and potential complications of harvesting of the blood vessel. In the past, the harvesting was done through a continuous incision (e.g., along the leg) that exposed the full length of the desired vein section. The continuous incision had been necessary in order to provide adequate exposure for visualizing the vein and for introducing the surgical instruments to sever, cauterize and ligate the tissue and side branches of the vessel.

A more recent development has been a minimally-invasive technique that employs a small incision for locating the desired vessel and for introducing one or more endoscopic devices into the small incision.

The current technology for minimally invasive vessel dissecting and harvesting used such devices as bipolar scissors, bipolar cutter or ultrasonic tips to cauterize the vessels. Commercially available products for performing the endoscopic blood vessel harvesting procedure described above include the dissector device and the harvesting device that are sold together as the "VirtuoSaph™ Endoscopic Vein Harvesting System" from Terumo Cardiovascular Systems Corporation of Ann Arbor, Mich. Endoscopic vein harvesting systems are also shown in U.S. Pat. No. 6,660,016 to Lindsay, U.S. Pat. No. 7,077,803 to Kasahara et al., U.S. patent application publication Nos. 2005/0010242 and 2005/0192612 both in the name of Lindsay, and U.S. patent application publication numbers 2005/0154257A1, 2005/0159764A1, 2005/0148817A1, 2005/0149094A1 in the name of Kasahara et al., all of which are incorporated herein by reference in their entirety.

It would be desirable to be able to have an additional apparatus and method to capture the vessel and to cut and/or cauterized the vessel and any branches extending from the vessel.

SUMMARY OF THE INVENTION

In one aspect, there is provided a device for dissecting a vessel from any surrounding vessel branch and for harvesting the vessel. The dissector/harvester device includes a capture tool and a sealing tool. The capture tool is at least partially co-axially positioned around the vessel to be harvested to temporarily hold the vessel.

In certain embodiments, the capture tool has a capture tube and a capture ring at a distal end of the capture tube. The capture ring is at least partially co-axially positioned around the vessel to at least temporarily hold the vessel. The sealing tool has a sealing tube and a sealing ring at a distal end of the sealing tube. The sealing ring receives a second and adjacent portion of the vessel. The sealing tool is capable of being at least axially movable with respect to the capture tool. Also, the sealing tool is capable of cauterizing a branch from the vessel and sealing the cauterized branch.

In certain embodiments, at least a portion of the sealing tool is capable of being pivotably movable with respect to the capture tool.

Also, in certain embodiments, the capture ring defines a first inner open space configured to receive a first portion of the vessel. The sealing tool defines a second inner open space configured to receive a second and adjacent portion of the vessel. In certain embodiments, the sealing ring and the capture ring each has at least one generally mating surface whereby, when the sealing ring is adjacent to the capture ring, the generally mating surfaces are configured to sever the branch or vessel.

Various objects and advantages of this invention will become apparent to those skilled in the art from the following detailed description of the preferred embodiment, when read in light of the accompanying drawings.

BRIEF DESCRIPTION OF THE DRAWINGS

FIG. 1 is a structure diagram, partially in phantom, showing a perspective view of a ring dissector/harvester device in an open position.

FIG. 1A is a structure diagram, partially in phantom, showing a plan view of a ring dissector/harvester device in a closed and engaged position.

FIG. 2 is a structure diagram, partially in phantom, showing a perspective view of a ring dissector/harvester device in a rotated position prior to cauterizing a blood vessel branch.

FIG. 2A is a structure diagram, partially in phantom, showing a perspective view of a ring dissector/harvester device in a rotated position subsequent to cauterizing a blood vessel branch.

FIG. 3 is a structure diagram, showing a perspective view of a ring dissector/harvester device within an endoscopic dissecting/harvesting device.

FIG. 4 is a structure diagram, showing a perspective view of a ring dissector/harvester device extended from an endoscopic dissecting/harvesting device.

DETAILED DESCRIPTION OF THE PREFERRED EMBODIMENT(S)

Referring first to FIGS. 3 and 4, structure diagrams of an endoscopic dissecting/harvesting device 2 having an endoscope 8 and a ring dissector/harvester device 10 for dissecting and/or harvesting a vessel are generally shown. In the embodiment shown, the ring dissector/harvester device 10 is longitudinally positioned in a sheath 4.

The ring harvester/dissector device 10 includes a capture tool 20 and a sealing tool 30, as further explained below. Prior to use, when the dissector/harvester device 10 is in a stored position, the capture tool 20 and sealing tool 30 are in alignment within an annular space 6 defined by the sheath 4. As further described below, when in the stored position, the capture tool 20 and the sealing tool 30 do not block the endoscope from providing a clear view of the area being dissected. Subsequently, in use, the capture tool 20 and the sealing tool 30 are rotated about their longitudinal axes to a position at least partially outside of the annular space 6, as shown in FIG. 4. In certain embodiments, the capture tool 20 and the sealing tool are at least partially radially displaced from the annular space 6 in the sheath 4.

It is to be understood that the endoscopic dissecting/harvesting device 2 can include and/or be connected to, for example: a monitor such as a display device, a camera control unit, a camera device, a light source device, a light guide, and an insufflation/gas feed device.

Referring now in particular to the ring dissector/harvester device 10, as best shown in FIGS. 1, 1A, 2 and 2A, the ring dissector/harvester device 10 generally includes the capture tool 20 and the sealing tool 30 for at least temporarily securing and holding a vessel and for simultaneously cauterizing the vessel and/or branch from a vessel.

The capture tool 20 includes an elongated capture tube 22 and a capture ring 24 that is positioned at a distal end 26 of the elongated capture tube 22. The capture ring 24 generally extends from the distal end 26 at an angle with respect to an axis through the capture tube 22. In certain embodiments, the capture ring 24 can be at a substantially right angle with respect to the capture tube 22. In other embodiments, the capture ring 24 can be at an angle other than a right angle.

In the embodiment shown, the capture ring 24 has a generally circular shape; however, in other embodiments, the capture ring 24 can have a different shaped loop, including, for example, oval, elliptical, triangular, and the like. The capture ring 24 has a first end 24a and a second and opposing end 24b. The first and second ends 24a and 24b are in a spaced apart relationship such that a narrow opening or gap 27 is formed between the first and second ends 24a and 24b. In certain embodiments, the first and second ends 24a and 24b are in a co-planar relationship. In certain embodiments, the capture ring 24 is mounted on the capture tube 22 at a point that is directly opposed to the gap 27.

The capture ring 24 defines an inner open space 28 for receiving an axially extending portion of the vessel V. During use, the capture ring 24 is pivotably rotated out of the annular space 6. The capture ring 24 is maneuvered by the physician who co-axially positions the capture ring 24 around a vessel to be harvested. The vessel is thus maneuvered to a position between the ends 24a and 24b and into the gap 27. The vessel V is then substantially encircled or retained in the inner open space 28.

The sealing tool 30 includes an elongated sealing tube 32. At least a portion of the sealing tube 32 is co-axially positioned within the capture tube 22 of the capture tool 20. The sealing tube 32 has a desired cross-sectional shape, such as, for example, round shown in FIG. 1, that allows the sealing tube 32 to be circumferentially rotated about a longitudinal axis A extending therethrough. In certain embodiments, the sealing tube 32 can be rotated in a 360° manner with respect to the capture tube 22.

The sealing tool 30 includes a sealing ring 34 that is positioned at a distal end 36 of the sealing tube 32. The sealing ring 34 is positioned at an angle with respect to the longitudinally axis through the sealing tube 32. In certain embodiments, the sealing ring 34 can be at a substantially right angle with respect to the sealing tube 32. In other embodiments, the sealing ring 34 can be at an angle other than a right angle.

In the embodiment shown, the sealing ring 34 has a generally circular shape; however, in other embodiments, the sealing ring 34 can have a different shaped loop, including, for example, oval, elliptical, triangular, and the like. The sealing ring 34 has a first end 34a and a second and opposing end 34b. The first and second ends 34a and 34b are in a spaced apart relationship such that a narrow opening or gap 37 is formed between the first and second ends 34a and 34b. In certain embodiments, the first and second ends 34a and 34b are in a co-planar relationship. Also, in certain embodiments, the sealing ring 34 can be mounted on the sealing tube 32 at a point that is directly opposed to the gap 37.

The sealing ring 34 defines an inner open space 38 for receiving an adjacent axially extending portion of the vessel V such that the sealing ring 34 can be co-axially positioned around a vessel to be harvested. Similarly, during use, the sealing ring 34 is pivotably rotated out of the annular space 6. The sealing ring 34 is also maneuvered by the physician who co-axially positions the sealing ring 34 around a vessel to be harvested. The vessel is thus maneuvered to a position between the ends 34a and 34b and into the gap 37. The vessel V is then substantially encircled or retained in the inner open space 38.

In certain embodiments, at least a portion of the capture ring 24 and at least a portion of the sealing ring 34 are in a generally parallel relationship with respect to each other. In certain embodiments, the sealing ring 34 and the capture ring 24 each has at least one generally mating surface 35 and 25, respectively, whereby, when the sealing ring 34 is adjacent to the capture ring 24, the generally mating surfaces 35 and 25, respectively, are configured to cauterize the branch or vessel, as further described below.

Also, both the capture tube 22 and the sealing tube 32 have proximal ends 23 and 33, respectively, which can be operatively connected to a handle (not shown).

Prior to use, at least a portion of the sealing tube 32 is co-axially positioned within the capture tube 22. Thereafter, in operation, the endoscopic dissecting/harvesting device 2 is first positioned within an initial incision in a patient. The dissector/harvester device 10 is generally aligned in a generally parallel relationship to the vessel V to be harvested, as shown in FIG. 1.

The capture tool 20 and the sealing tool 30 are pivotably out of the annular space 6 and the capture ring 24 and the sealing ring 34 are moved to a co-axial position around the vessel V. The sealing tube 32 is axially extended from the capture tube 22. If needed, the sealing tube 32 is rotated in the capture tube 22 such that the seal ring 34 pivots with respect to the capture ring 24. As best seen in FIG. 1A, the sealing ring 34 is pivotably movable with respect to the capture ring 24 such that the ring dissector/harvester device 10 is capable of releasably holding, and subsequently cauterizing, the branch B when the capture ring 24 and the sealing ring 24 are in a non-aligned position with respect to each other.

The sealing tube 32 is manipulated to extend the sealing ring 34 onto a far side of a vessel branch B that extends from the vessel V. A first portion V-1 of the vessel V is maneuvered into the opening 27 of the capture ring 24. As best seen in FIGS. 2 and 2A, the capture ring 24 has a first inner surface 24c that is configured to at least temporarily hold the first portion V-1 of the vessel V within the capture ring 24 without substantially damaging the first portion V-1 of the vessel V. An adjacent and second portion V-2 of the vessel V is maneuvered into the opening 37 of the sealing ring 34. The sealing ring 34 has a first inner surface 34c that is configured to at least temporarily hold the second portion V-2 of the vessel V within the sealing ring 34 without substantially damaging the first portion V-1 of the vessel V. As shown by the arrow in FIG. 2A, the sealing ring 34 can be axially movable with respect to the capture ring 24 such that the sealing ring 34 and the capture ring 24 can releasably hold the branch B without damaging the vessel V or the branch B.

Once the branch is positioned within the inner spaces 28 and 38, respectively, of the capture ring 24 and sealing ring 34, the sealing tube 32 is retracted in an axial direction. The sealing ring 34 is brought into close alignment with the capture ring 24. The sealing ring 34 is activated, thereby severing and/or cauterizing the branch B. The sealing ring 34 can be activated and/or advanced and retracted by one or more mechanisms (not shown) on the dissector/harvester device 10.

To continue with the dissecting and harvesting procedure, the ring harvester/dissector device 10 retains the vessel V being harvested within the inner open space 28 within the capture ring 24. The sealing ring 24 is then moved to a further extended position toward another vessel branch that might be attached to the vessel. The sealing ring 34 is again manipulated, by pivoting about the sealing tube 32, if necessary. A further portion of the vessel is maneuvered within the gap 37 and is held in the opening 38 within the sealing ring 34. The sealing ring 34 is again axially moved in a direction toward the capture ring 24 and the sealing ring 34 is activated and/or engaged for cauterizing each branch to prepare the vessel for removal.

In the embodiment shown in FIG. 1, the capture tool 20 and the sealing tool 30 are operatively connected to a power supply 40. At least one of the capture ring 24 and the sealing ring 24 acts as an electrode and is configured for being electrically energized to cauterize the branch B. In another embodiment, the capture ring 24 can be a ground for the sealing ring 34 that uses a high frequency alternating voltage to cauterize the vessel. In yet other embodiments, the sealing tool 30 can be an ultrasonic cauterizing tool or a bipolar electrocautery tool.

In certain embodiments, the capture tool 20 is substantially stationary with respect to the sealing tool 30. It should be understood that, in certain other embodiments, both the capture ring 24 and the sealing ring 34 can be axially moveable with respect to each other.

In one method, the ring dissector/harvester device 10 is pivotably moved in a radial direction from a first position within the annular space 6 within the sheath 4 to a second external position. At least a portion of each of the capture tool and the sealing tool are positioned around the vessel. The sealing tool is positioned in a spaced apart relationship with respect to the capture tool so that at least one vessel branch is in the spaced apart area between the sealing tool and the capture tool. The sealing tool is moved to a closed position substantially adjacent to the capture tool whereby the vessel branch is substantially captured between the sealing ring 34 and the capture ring 24. One or more of the capture ring 24 and/or sealing ring 34 is engaged to cauterize (and then sever) the captured branch from the vessel.

Also, in certain embodiments, one or more of the capture ring 24 and sealing ring 24 can be made of a shape retention memory alloy that is capable of constricting when a supply of electricity is supplied to the alloy. In such embodiment, the capture ring 24 and/or the sealing ring 34 can have smaller diameters than as generally depicted in the drawings.

In accordance with the provisions of the patent statutes, the principle and mode of operation of this invention have been explained and illustrated in its preferred embodiment. However, it must be understood that this invention may be practiced otherwise than as specifically explained and illustrated without departing from its spirit or scope.

What is claimed is:

1. A device for dissecting a vessel from any surrounding vessel branch and/or for harvesting the vessel, the device including:
   a capture tool having a capture tube and a capture ring at a distal end of the capture tube, the capture ring being configured to be at least partially positioned around a first portion of the vessel and to releasably hold the first portion of the vessel within the capture ring; and
   a sealing tool having a sealing tube and a sealing ring at a distal end of the sealing tube, the sealing ring being configured to receive a second and adjacent portion of the vessel and to releasably hold the second portion of the vessel within the sealing ring,
   the sealing tool being capable of being at least axially movable with respect to the capture tool, the sealing ring and the capture ring being configured to: i) releasably hold the branch, and ii) to cauterize a branch from the vessel and to at least seal the cauterized branch;
   wherein at least the sealing ring is configured to be reduced in diameter.

2. The device of claim 1, wherein at least a portion of the sealing tool is capable of being pivotably movable with respect to the capture tool.

3. The device of claim 1, wherein the capture ring defines a first inner open space configured to receive the first portion of the vessel; and, wherein the sealing tool defines a second inner open space configured to receive the second and adjacent portion of the vessel.

4. The device of claim 1, wherein the sealing ring and the capture ring each has at least one generally mating surface whereby, when the sealing ring is adjacent to the capture ring, the generally mating surfaces are configured to cauterize the branch or vessel.

5. The device of claim 1, wherein the sealing tool is configured to receive a supply of energy to cauterize the branch and vessel.

6. The device of claim 1, wherein the sealing tool comprises an ultrasonic cauterizing tool.

7. The device of claim 1, wherein the sealing tool comprises an electrocautery tool.

8. The device of claim 1, wherein the capture tool is substantially stationary with respect to the sealing tool.

9. The device of claim 1, wherein the sealing ring is configured to be pivotably movable with respect to the capture ring.

10. The device of claim 1, wherein the capture ring extends at substantially a right angle with respect to the capture tube, and the sealing ring extends at substantially a right angle to the sealing tube,
    whereby at least a portion of each of the capture ring and the sealing ring are in a parallel relationship with respect to each other.

11. The device of claim 1, wherein the capture ring and the sealing ring have generally open circular shapes.

12. The device of claim 1, wherein at least a portion of the sealing ring is configured to be constricted around at least a portion of the vessel.

13. A device for dissecting a vessel from any surrounding vessel branch and/or for harvesting the vessel, the device including:
    a capture tool having a capture tube and a capture ring at a distal end of the capture tube, the capture ring being configured to be at least partially positioned around a first portion of the vessel to be harvested,
    the capture ring having a first inner surface configured to at least temporarily hold the first portion of the vessel within the capture ring without substantially damaging the first portion of the vessel; and, a sealing tool having a sealing tube and a sealing ring at a distal end of the sealing tube, the sealing ring being configured to receive a second and adjacent portion of the vessel, the sealing ring having a second inner surface configured to at least temporarily hold the second portion of the vessel within the sealing ring, the sealing ring being capable of being at least axially movable with respect to the capture ring, the capture ring and the sealing ring being capable of cauterizing a branch positioned between the capture ring and the sealing ring;

wherein the sealing ring and the capture ring each has at least one generally planar surface whereby, when the sealing ring is adjacent to the capture ring; and wherein the generally planar surfaces are configured to releasably hold the branch or vessel without substantially damaging the branch or vessel.

14. The device of claim 13, the sealing ring configured to be pivotably movable with respect to the capture ring, whereby the device is capable of releasably holding, and subsequently cauterizing, the branch when the capture ring and the sealing ring are in a non-aligned position with respect to each other.

15. The device of claim 13, the inner capture ring defining a first inner open space configured to receive the first portion of the vessel; and, the sealing tool defining a second inner open space configured to receive the second and adjacent portion of the vessel;

the device being capable of releasably holding, and subsequently cauterizing the branch when the first inner open space of the capture ring and the second inner open space of the sealing ring are in a non-aligned position with respect to each other.

16. The device of claim 13, wherein the capture ring extends at substantially a right angle with respect to the capture tube, and the sealing ring extends at substantially a right angle with respect to the sealing tube, whereby at least a portion of each of the capture ring and the sealing ring are in a parallel relationship with respect to each other.

17. The device of claim 13, wherein the capture ring and the sealing ring have generally open circular shapes.

18. A device for dissecting a vessel from any surrounding vessel branch and/or for harvesting the vessel, the device including:

a capture tool having a capture tube and a capture ring at a distal end of the capture tube, the capture ring being configured to be at least partially positioned around a first portion of the vessel and to releasably hold the first portion of the vessel within the capture ring; and a sealing tool having a sealing tube and a sealing ring at a distal end of the sealing tube, the sealing ring being configured to receive a second and adjacent portion of the vessel and to releasably hold the second portion of the vessel within the sealing ring, the sealing tool being capable of being at least axially movable with respect to the capture tool, the sealing ring and the capture ring being configured to: i) releasably hold the branch, and ii) to cauterize a branch from the vessel and to at least seal the cauterized branch;

wherein at least the sealing ring is made of a shape memory alloy.

19. The device of claim 18, wherein at least a portion of the sealing tool is capable of being pivotably movable with respect to the capture tool.

20. The device of claim 18, wherein the capture ring defines a first inner open space configured to receive the first portion of the vessel; and, wherein the sealing tool defines a second inner open space configured to receive the second and adjacent portion of the vessel.

\* \* \* \* \*